US008176785B2

(12) United States Patent
David et al.

(10) Patent No.: US 8,176,785 B2
(45) Date of Patent: May 15, 2012

(54) METHOD AND DEVICE FOR DETECTING WATER IN A CELLULAR STRUCTURE

(75) Inventors: Jacques David, Montastruc (FR);
Tan-Hoa Vuong, Carcassonne (FR);
Bastien Roucaries, Balma (FR);
Bertrand Nogarede, Coursan (FR);
Raymond Crampagne, Toulouse (FR)

(73) Assignee: Institut National Polytechnique de Toulouse, Toulouse (FR)

( * ) Notice: Subject to any disclaimer, the term of this patent is extended or adjusted under 35 U.S.C. 154(b) by 318 days.

(21) Appl. No.: 12/663,160

(22) PCT Filed: Jun. 2, 2008

(86) PCT No.: PCT/EP2008/056796
§ 371 (c)(1),
(2), (4) Date: Feb. 24, 2010

(87) PCT Pub. No.: WO2008/148740
PCT Pub. Date: Dec. 11, 2008

(65) Prior Publication Data
US 2010/0162818 A1 Jul. 1, 2010

(30) Foreign Application Priority Data
Jun. 5, 2007 (FR) ...................................... 07 55459

(51) Int. Cl.
*G01N 22/04* (2006.01)
*G01F 23/00* (2006.01)
(52) U.S. Cl. ...................................... 73/592; 324/76.11
(58) Field of Classification Search .................... 73/592, 73/584, 596; 324/76.11
See application file for complete search history.

(56) References Cited

U.S. PATENT DOCUMENTS 4,899,844 A * 2/1990 Katahara et al. ............... 181/106
6,120,662 A * 9/2000 Edwards et al. ............... 204/400
(Continued)

FOREIGN PATENT DOCUMENTS
EP 0938653 A1 9/1999
(Continued)

OTHER PUBLICATIONS

Laplante G. et al., "Detection of water ingress in composite sandwich structures: a magnetic resonance approach," NDT & E International, Butterworth-Heinemann, Oxford,, GB, vol. 38, No. 6, Sep. 2005, pp. 501-507.

*Primary Examiner* — J M Saint Surin
(74) *Attorney, Agent, or Firm* — Im IP Law PLLC; C. Andrew Im

(57) ABSTRACT

The invention relates to the detection of liquid in a cavity of a structure, e.g. a sandwich-structure cell with honeycomb core and carbon fiber composite coating. The structure is subjected to a mechanical vibration, at a frequency $f_m$ in the audible range, by an excitation wave, the area being explored is subjected to an incident electromagnetic wave and the reflected electromagnetic wave is analyzed to deduce therefrom the presence or the absence of liquid in cavities. The Faraday wave induced on the surface of the liquid in the cavity comprises subharmonic frequencies of $f_m$ which modulate the reflected electromagnetic wave and make it possible to identify the presence of liquid. A detection apparatus comprises an excitation wave generation device for generating the vibration excitation wave, an electromagnetic wave generation device for generating the incident electromagnetic wave, a measuring device for detecting and measuring the reflected electromagnetic wave, and a signal processor.

16 Claims, 3 Drawing Sheets

U.S. PATENT DOCUMENTS

| | | | |
|---|---|---|---|
| 7,429,354 B2* | 9/2008 | Andersson et al. | 422/506 |
| 7,578,567 B2* | 8/2009 | Zhang et al. | 347/7 |
| 2004/0183550 A1 | 9/2004 | Fehrenbach et al. | |
| 2005/0156607 A1 | 7/2005 | Okamura | |
| 2010/0163130 A1* | 7/2010 | Laberge et al. | 137/827 |

FOREIGN PATENT DOCUMENTS

| | | |
|---|---|---|
| FR | 2880424 A1 | 7/2006 |
| JP | 62024134 A | 2/1987 |
| JP | 05188041 A | 7/1993 |

* cited by examiner

METHOD AND DEVICE FOR DETECTING WATER IN A CELLULAR STRUCTURE

RELATED APPLICATIONS

This application is a §371 application from PCT/EP2008/056796 filed Jun. 2, 2008 which claims priority from French Patent Application No. 07 55459 filed Jun. 5, 2007, each of which is herein incorporated by reference in its entirety.

TECHNICAL FIELD OF THE INVENTION

The present invention falls within the field of nondestructive testing of structures. In particular, the invention relates to the detection and location of liquids in internal cavities of structures.

BACKGROUND OF THE INVENTION

In the field of structures in mechanical constructions, the objective of producing structures as light as possible, while still ensuring that they are strong and rigid, often results in relatively highly loaded structural parts that include cavities.

The form and composition of such structural parts are very varied, one of the most common forms corresponding to what are called "sandwich" structures having a honeycomb cellular core.

A cellular-core sandwich structure 1, as shown in cross section in FIG. 1, generally comprises a core 2 formed from hollow cells 12, a priori containing air, having on each of its faces, namely the bottom face and the top face, a solid and strong skin panel, respectively 4, 3.

This type of structure, because of its very favorable rigidity-strength/weight ratio, is used particularly in aeronautical constructions.

In one particular embodiment, which is also well known, the skin panels 3, 4 of the sandwich structure are made of composites comprising fibers—glass fiber, aramid fiber, carbon fiber, etc.—held in place in a cured resin, and the hollow cells 12 of the cellular core 2 are formed by means of walls produced in a sheet material shaped so as to define the cells in the form of a usually regular lattice. When this lattice consists of cells of hexagonal cross section, the expression "honeycomb" is generally used.

In most cases, the materials used for the skin panels and for the walls of the cells are relatively impervious to common fluids, resulting in a situation in which each cell constitutes a substantially closed and sealed cavity.

One drawback of this type of structure stems from the fact that the hollow cells are liable to fill up to a greater or lesser extent with water, without this water being able to be removed naturally. This has the effect, on the one hand, of unnecessarily increasing the weight of the structure, intended to be a lightweight structure, and, on the other hand, of reducing, through various physicochemical actions, the strength of the structure by impairing the specific mechanical properties of the materials used in producing the structure or by impairing the quality of the bonding between the various assembled elements, in particular between the cellular material and the skin panels.

The presence of water, or in general of liquid, in hollow cells which is generally considered to be a major defect of the structure, usually cannot be predicted and, whatever the causes of liquid being present—water formation process during manufacture of the structure or subsequent liquid penetration into cells—it is essential to detect the presence of the liquid in cells, to locate where the liquid is and to quantify the amount thereof so as to carry out the necessary actions for removing the largest possible amount of this liquid.

The detection of liquids in such cavitied structures is a long-standing problem. However, the conventional approaches suffer from major drawbacks.

Apart from visual inspections, limited to cases in which the materials used are sufficiently transparent for the liquid in a cell to be observed by optical means, the methods that have been used for the longest time and are well known to those skilled in the art are based on the principle of acoustic detection.

Echographic methods based on this principle are particularly well suited for continuous compact media. In the case of cellular—low-density cavitied—structures, the transmission of an acoustic wave is difficult and is unable to discriminate with the necessary precision the presence of liquid.

A purely acoustic, derived method, suitable for detecting the level of a liquid in a closed space—in this case a bottle—is disclosed in the patent published under the number EP 0 938 653. According to that patent, vibrations are induced in the bottle by means of a magnetic field and an acoustic signal in response to the vibrations is received by a microphone.

The presence and level of liquid in the bottle can be deduced from the characteristics of this received acoustic signal. However, in the case of highly cavitied materials, such as those considered here, this approach does not allow the presence of water in the cavities to be effectively detected because of the weakness of the echo.

Other methods aimed particularly at detecting the presence of water in cellular-core sandwich structures using other physical principles have also been imagined.

According to one of these other methods, since water has thermodynamic characteristics that are very different from the materials in which the presence of water is sought, it has been proposed to produce a thermographic image of a part subjected to temperature variation. In this case, the zones corresponding to water being present vary in temperature less rapidly than the zones where there is no water, because of the differences in thermal inertia between the water and the materials of the part, a thermographic image being capable of detecting the differences in surface temperatures and therefore zones containing water.

Such methods, one example of which is disclosed in the patent published under the number JP 62024134, have however the drawback, on the one hand, of usually requiring the part to be removed, in order for it to be investigated, and, on the other hand, of requiring substantial means for cooling or heating the part under conditions suitable for the measurements to be carried out.

According to another method, the presence of water in the cells is detected by means of electromagnetic microwaves, the propagation of which is modified in the presence of water.

However, the use of electromagnetic microwaves is constricting in terms of the precautions to be taken to protect personnel when the energy level used is significant.

Furthermore, difficulties arise in the case of sandwich structures using skin panels made of a carbon-fiber-based material or having a metallized surface, for example one metallized by means of a bronze mesh, which is the situation for many parts.

In the case of a structure based on carbon fibers, the carbon of the skin panels induces high losses and the signal-to-noise ratio is extremely unfavorable for detection.

When a bronze metallization mesh covers a surface, which is frequently the case for modern aeronautical materials, the skin panels are electrically conducting and prevent any measurements of the dielectric type.

To solve this problem, the solution described in the patent published under the number FR 2 880 424 describes a detection system using electromagnetic microwaves that includes antennas placed in the cellular material of a sandwich panel between the two skin panels. This solution, which is applicable in the case of carbon-fiber-based skin panels, does however require the parts to be modified in order to install the antennas. As a result, the parts are more complex, weaker and heavier, and the solution cannot be easily used for many existing parts or on parts that would not have been provided with these antennas during their manufacture, for cost reasons or for other reasons.

In general, the presence of a bronze mesh prevents any approach of the type in which the level of fluid in the cavities is measured by a radar device (in the radio, microwave or millimeter frequency ranges), since the bronze mesh reflects most of a radio wave in these frequency ranges. To alleviate this drawback, it is usually necessary to reduce the working frequency, but this has the effect of dramatically degrading the precision of the measurements and prevents a measurement of the liquid level from being carried out with sufficient precision.

OBJECT AND SUMMARY OF THE INVENTION

The objective of the present invention is specifically to alleviate the difficulties encountered by the techniques of the prior art for detecting a liquid in cavities of a structure by coupling a vibratory excitation of the structure in the acoustic range with electromagnetic detection of the vibratory response of the structure.

Thus, according to the method of detecting the presence of a liquid in a cavity of a structure, in which the structure is subjected to a mechanical vibration by means of an excitation wave and is subjected to an incident electromagnetic wave in a zone of said structure in which the presence of the liquid in a cavity is sought.

Finally, a reflected electromagnetic wave, reflection of the incident wave on elements of the structure, is analyzed so as to deduce therefrom the presence or absence of liquid in cavities, the reflected wave having characteristics that are modified according to whether or not liquid is present in the cavities.

To create a Faraday wave on the surface of a liquid present in a cavity of the structure, which is perfectly distinct from the frequencies at which the structure responds in the absence of liquid, one component of the excitation wave is generated by an approximately sinusoidal vibratory excitation of frequency $f_m$, preferably in the acoustic range, capable of initiating an induced oscillation of the surface of the liquid in a cavity at a subharmonic frequency of the excitation frequency $f_m$.

To improve the sensitivity of the method, one component of the excitation wave is also generated by a vibratory excitation of frequency $f_{m2}$ shifted relative to the frequency $f_m$, thereby enabling a standing wave pattern to be created on the surface of the liquid and increasing the vibratory response of the liquid relative to the response of the structure.

To improve the signal-to-noise ratio, the frequency of one of the components of the excitation wave is advantageously modulated and more particularly is modulated by a white or psuedo-white noise.

Because of the very different frequencies of the vibratory responses of the liquid present in cavities from that of the structure, the method makes it possible, with a high signal-to-noise ratio, to deduce the presence of liquid from the detection of predefined spectral lines in the spectrum of the reflected wave.

In particular, the presence of liquid is deduced from the detection of at least one predefined spectral line in the spectrum of the reflected wave corresponding to a subharmonic of frequency $f_m/2$ and/or $f_{m2}/2$ of the excitation frequency $f_m$ and/or $f_{m2}$ respectively.

According to the invention, a device suitable for implementing the method of detecting the presence of liquid in a cavity of a structure comprises:

first means for generating at least one vibratory mechanical excitation wave in the structure;

second means for generating an incident electromagnetic wave in a zone of the structure in which the presence of a liquid is sought;

third means for measuring an electromagnetic wave reflected by the structure receiving the incident wave; and fourth, processing and/or display means capable of demonstrating the presence in a spectrum of the reflected wave of at least one spectral line characteristic of an induced wave on a surface of a liquid contained in a cavity of the structure by the mechanical excitation wave.

To produce a compact device, at least for a probe part, the probe comprises a torus using piezoelectric technology capable of mechanically vibrating so as to create the mechanical excitation wave at a frequency $f_m$, or at a frequency $f_m$ and at a frequency $f_{m2}$ shifted relative to the frequency $f_m$.

Advantageously, the hollow part of the torus is exploited so as to provide:

an antenna for transmitting and receiving the electromagnetic waves; and/or all or part of the supply electronics for the piezoelectric component; and/or all or part of the supply electronics for the antenna for transmitting the incident electromagnetic wave; and/or all or part of the detection electronics for detecting the reflected electromagnetic wave; and/or all or part of the signal processing electronics.

BRIEF DESCRIPTION OF THE DRAWINGS

One method of implementation and one embodiment of the invention will be described in detail with reference to the figures, which show:

FIG. 1b: a simplified diagram illustrating an improvement of the method and the device shown in FIG. 1a;

DETAILED DESCRIPTION OF THE EMBODIMENTS

Figure 1A:
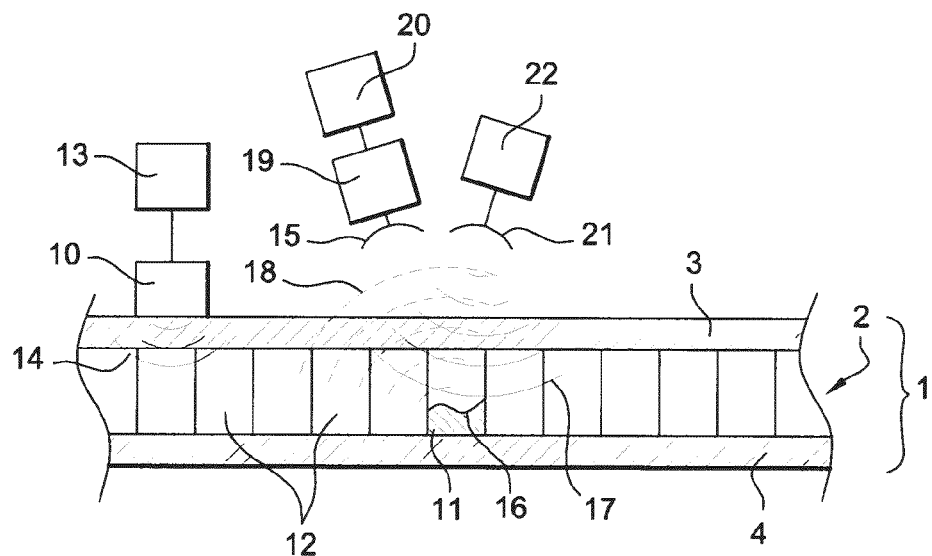
FIG. 1a: a simplified diagram of the method of the invention and a device according to the invention.

The present invention, the principle of which is illustrated in FIG. 1a, is used for detecting the presence of a liquid 11, for example water, in a structure 1 having at least one cavity 12.

For the requirements of the detailed description of one way of implementing the method according to the invention and that of one embodiment of a device according to the invention, said structure having at least one cavity is represented by a structure 1 of a panel, which is substantially flat on the scale of a zone in question, comprising a cellular core 2 and skin panels—a top skin panel 3 and a bottom skin panel 4—on the faces of the cellular core 2.

Each cell 12 of the core, closed at its ends by the top and bottom skin panels, constitutes a cavity.

The panel 1 comprises in practice a multitude of cavities 12, which makes the problem of detecting a liquid in some of the cavities more complicated in practice since it is then necessary to locate the cavity or cavities in which the liquid is present.

A panel having such a structure, in which the cells have regular hexagonal cross sections, is generally referred to as a honeycomb core sandwich panel.

However, the choice of such a frequently used structure to describe the invention is not limiting.

As is known, the skin panels 3, 4 of the panel in question are made of a composite formed from fibers held in place in a cured resin, for example glass fibers or carbon fibers held in place by a cured aramid resin, and the walls forming the cells of the honeycomb are made of a composite, in principle a less expensive one than the carbon-fiber-based materials, for example based on glass fibers or based on thin sheets of an organic material.

According to the method of the invention, the structure 1 to be inspected, comprising numerous cavities 12, some of which are liable to contain a liquid 11, is mechanically excited so as to vibrate.

The mechanical excitation is preferably produced by means of a sinusoidal excitation of frequency $f_m$ falling within the acoustic frequency range.

The structure 1 to be inspected is mechanically excited in such a way that an acoustic wave 14, called excitation wave, propagates in the structure 1.

When the excitation wave 14 reaches a cell 12 containing a liquid 11, for example water in liquid form, said wave creates on the free surface of the water, by a nonlinear effect, a new wave 16, called induced wave, also known as a Faraday wave.

The induced wave 16 is predominantly a subharmonic at half that of the excitation wave, i.e. said induced wave is a wave of frequency $f_m/2$ that only fluid phenomena can generate.

Furthermore, the structure 1, in a zone in which the presence of liquid is sought, is subjected to an electromagnetic wave 17.

The electromagnetic wave 17 is preferably a sustained radar wave of the type of waves generated by means of a CW (continuous wave) radar.

The electromagnetic wave 17, called incident wave, is chosen with a frequency suitable for the materials making up the composition of the cellular structure and in particular according to the material of the skin panel lying between the source of the electromagnetic wave and the possible liquid that has to be detected, in such a way that said skin panel introduces only a reasonable attenuation, for example <120 dB.

In particular, when the cellular structure 1 is covered, on a face through which the incident wave 17 passes and/or through which a reflected wave that has to be observed passes, with electromagnetic shielding, for example a conducting mesh, care will be taken to chose the frequency of the incident wave 17 so as to prevent said incident frequency, and also the expected frequencies of a reflected wave, from corresponding to a forbidden frequency band for which the attenuation would be maximal.

As is known, the choice of frequency of the incident wave also results from a compromise between, on the one hand, keeping the losses in the materials of the structure 1 at an acceptable level for the measurement means employed—the losses, which are dependent on the material, increasing when the frequency increases—and, on the other hand, the desired spatial sensitivity, the resolution being better when the frequency is increased.

By taking these parameters for choosing a frequency of the incident wave 17 into consideration, it is possible, according to the method of the invention, to limit the power used for said incident wave to relatively low levels, limiting the physiological risks associated with electromagnetic radiations.

The incident wave 17 is reflected by the various elements that are present along its path and especially by the free surface of the liquid possibly present in a cell in order to form a reflected wave 18 modulated by the mechanical vibrations of said various elements.

When a liquid 11 is present in a cell, the wave 18 reflected by the surface of said liquid, subjected to the mechanical excitation frequency $f_m$, is modulated not only by the vibrations of the structure due to the excitation wave 14, at the frequency $f_m$, i.e. vibrations at the frequency $f_m$ and multiple harmonics of f, but also those due to the induced wave 16 at said surface of said liquid with subharmonic frequencies and in particular the frequency $f_m/2$.

By processing a measurement of the reflected wave it is possible to extract a useful signal for identifying the presence or absence of liquid in the cell or cells subjected to the incident wave 17.

This processing comprises an analysis of the baseband spectrum of the reflected electromagnetic wave in order to detect a possible subharmonic of the excitation frequency.

One advantage of the method stems from the fact that, on the one hand, the electromagnetic wave, unlike acoustic waves, is insensitive to the presence of acoustic vacancies characteristic of cellular materials and, on the other hand, the consequences of the original excitation at the frequency $f_m$ and of the higher-order (second, third, fourth, etc.) harmonics due to the nonlinearities within the solids constituting the structure, may be effectively filtered out, since they are well separated in the spectrum of the sought frequencies of the induced wave.

The direct consequences are a sufficient power of the useful signal, so that it can be measured without any particular difficulty, and a very favorable signal-to-noise ratio.

The following equations illustrate how the reflected wave 18 is influenced by the presence of a liquid in a cell.

If the incident wave 17 is characterized by an emitted electromagnetic signal e(t), for example a sinusoidal signal of frequency $f_e$ and amplitude $E_e$, the signal is expressed as:

$$e(t) = E_e \times \exp(j \times 2 \times \pi \times f_e \times t)$$

where j is the imaginary unit and using the so called exponential notations, t being the time variable. The operator × corresponds to multiplication.

The reflected wave 18 is characterized by a signal s(t).

The signal $s_0(t)$ reflected by a stationary object corresponds to the emitted signal e(t) phase-shifted according to the electrical distance from the object T, i.e.:

$$s_0(t) = E_e \times \exp[jx(2\times\pi\times f_e \times t + T)] = E_e \times \exp(jx2\times\pi\times f_e \times t) \times \exp(j\times T)$$

When the signal s(t) is reflected by an object mechanically vibrating at a frequency $f_m$, the signal received is of the form:

$$s(t) = E_e \times \exp[jx(2\times\pi\times f_e \times t + a\times\sin(2\times\pi\times f_m \times t))] \times \exp(jx T)$$

in which expression a is a coefficient proportional to the mechanical amplitude with which the object vibrates.

This expression for the reflected signal is also expressed by means of k-order Bessel functions $J_k$:

$$s(t) = E_e \times \in xp(j \times T) \times \in$$
$$xp(j \times 2 \times \pi \times f_e \times t) \times \sum_{k=-\infty}^{\infty} [J_k(a) \times \in xp(2 \times \pi \times f_m \times t)]$$

This expression corresponds to a symmetrical spectrum of lines, centered on the frequency $f_e$.

Each line is separated from a neighboring line by a frequency $f_m$.

In the particular case of the panel 1 corresponding to the application of the method, the signal will a priori be reflected several times, in particular in the cavities.

In the absence of liquid in the cells, the signal therefore has the following form, noting the parameters associated with the various reflections by the index i:

$$s(t) = \Sigma_i [E_{e_i} \times \exp(jx2\times\pi\times f_e \times t) \times \exp(jxT_i) \times \exp(jxa_i \times \sin(2\times\pi\times f_m \times t))]$$

The spectrum of this signal again corresponds to a symmetrical spectrum of lines centered on the frequency $f_e$, each line of which is separated from an adjacent line by a distance $f_m$.

In the presence of a liquid in at least certain cells, the signal corresponding to the reflected wave contains a new term, due to the presence of the induced wave 16 on the surface of the liquid 11, of the form:

$$s(t) = E_{e_i} \times \exp[jx(2\times\pi\times f_e \times t + a\times\sin(2\times\pi\times f_m/2 \times t))] \times \exp(jx T)$$

assuming a subharmonic response of the liquid dominated by the half-frequency ½ subharmonic, the above expression also being expressed as:

$$s(t) = E_e \times \in xp(j \times T) \times \in$$
$$xp(j \times 2 \times \pi \times f_e \times t) \times \sum_{k=-\infty}^{\infty} [J_k(a) \times \in xp(j \times 2 \times \pi \times k \times f_m/2 \times t)]$$

The spectrum of this signal corresponds to a symmetrical spectrum of lines centered on the frequency $f_e$, each line of which is separated from an adjacent line by a distance $f_m/2$.

The presence of liquid 11 in a cell 12 is therefore demonstrated by the presence in the spectrum of the reflected wave 18 of lines at frequencies $f_m/2$, $3f_m/2$, $5f_m/2$, etc., which frequencies are absent in the case in which there is no liquid in the cells.

Figure 2A:
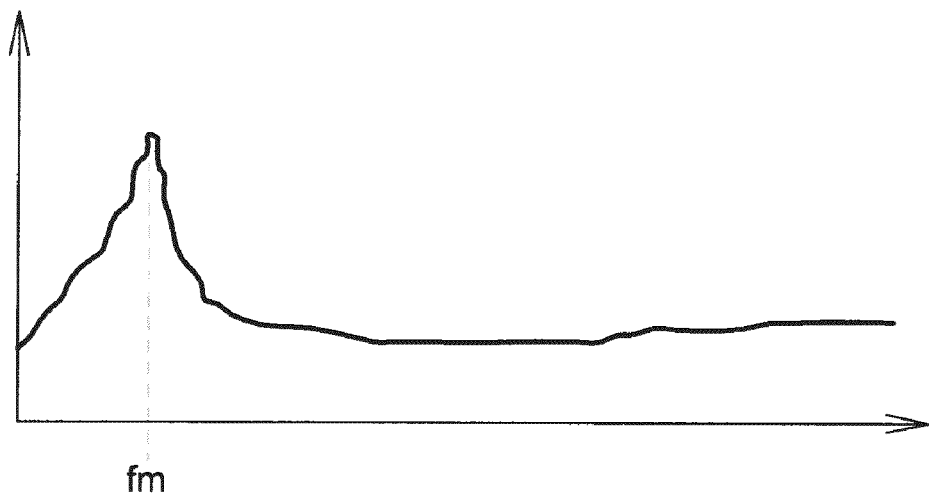
FIG. 2a: an illustration of an example of a reflected wave spectrum observed in a structure in the absence of liquid with a set-up of the type shown in FIG. 1a, the frequencies being plotted on the x-axis and the power on the y-axis.
Figure 2B:
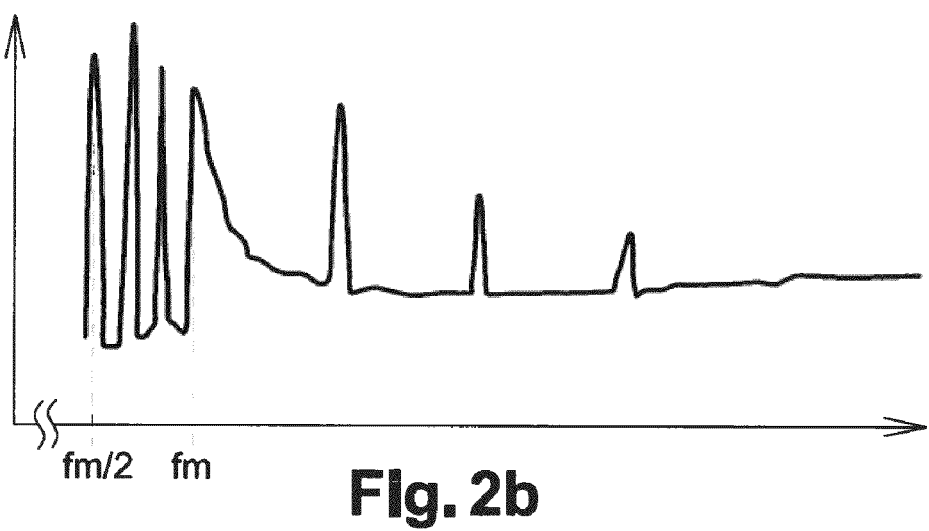
FIG. 2b: an illustration under the same conditions as in FIG. 2a of an example of a reflected wave spectrum observed in a structure in the presence of liquid in a cavity, the frequencies being plotted on the x-axis and the power on the y-axis.

FIG. 2a illustrates an example of an experimentally observed spectrum in the absence of a liquid in the cells and FIG. 2b illustrates an example of a spectrum in the presence of water in cells of a panel of a honeycomb sandwich structure.

In the spectrum of FIG. 2a, a spectral line is characteristic of the frequency $f_m$, and no subharmonics can be distinguished, unlike in the spectrum of FIG. 2b which shows subharmonics of the frequency $f_m$.

Figure 1B:
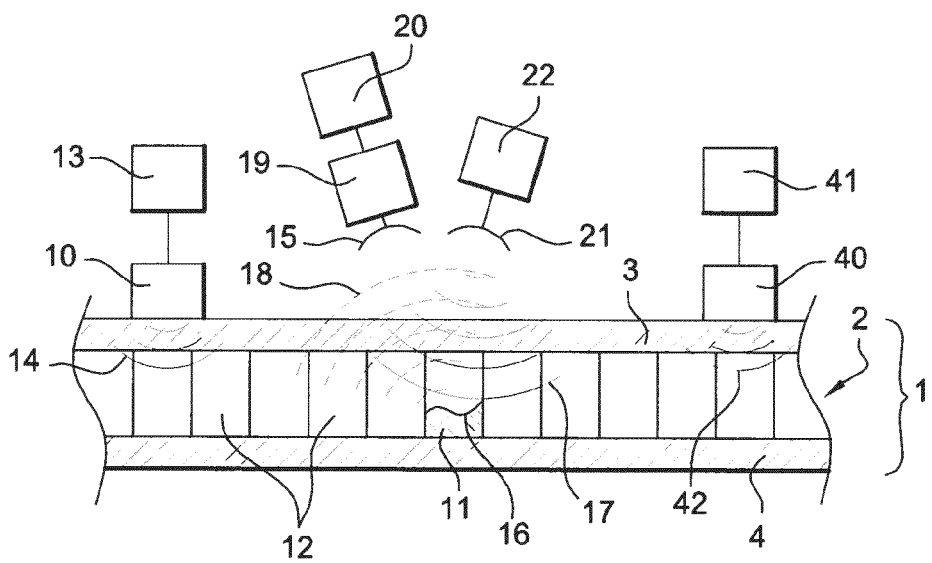

In an advanced form of the method according to the invention corresponding to the illustration in FIG. 1b, to improve the sensitivity of liquid detection, the structure 1 is excited in mechanical vibration by means of two frequencies, the frequency $f_m$ and a second frequency $f_{m2}$, said two frequencies being close together.

In fact it is known (see for example Thomas Besson and W. Stuart Edwards, "Two-frequency parametric excitation", Physical Review, July 1996) that setting a surface of a liquid into vibration using two frequencies produces a subharmonic stationary wave.

The mechanical excitation at the frequency $f_{m2}$ generates a wave 42 that propagates in the material 1 and interferes with the mechanical excitation wave 14 at the frequency $f_m$ in order to create an interference pattern on the surface of the liquid 11 when a cell 12 contains such a liquid.

The mechanical excitation signal corresponding to the frequency $f_{m2}$ may correspond to a pure sinusoidal signal or a modulated sinusoidal signal.

Figure 3:
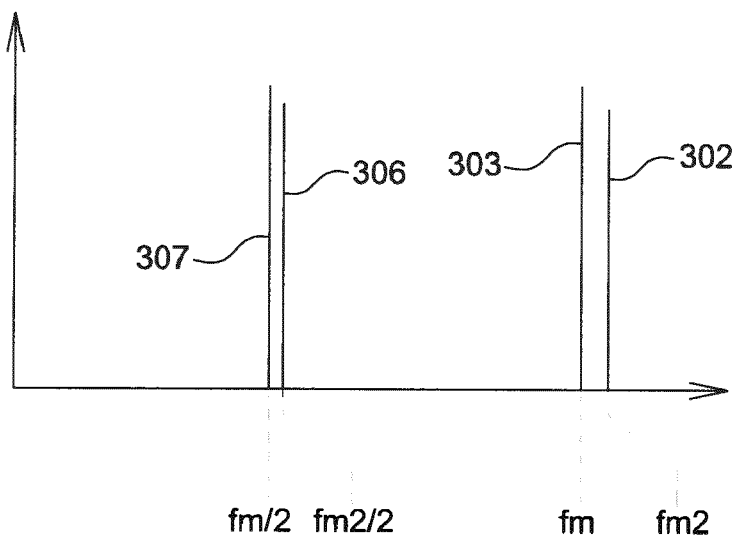
FIG. 3: an illustration of the spectrum of the reflected wave in the case of a dual-frequency set-up corresponding to the diagram shown in FIG. 1b.

FIG. 3 shows schematically in this case a spectrum received in baseband by the electromagnetic sensor.

Advantageously, the excitation signal corresponding to the frequency $f_{m2}$ is modulated by a white or psuedo-white (M-sequence) noise enabling signal processing methods of the autocorrelation type for improving the signal-to-noise ratio to be used.

In practice, the modulation by a M-sequence is capable of exciting nonlinear modes of the structure or of the fluid (parasitic mixing phenomenon). However, if the mechanical excitation frequencies are chosen in such a way that said frequencies are close together, i.e. $|f_{m2}-f_m| \ll f_m/2$, the bands due to the frequencies mixing do not overlap the ½ harmonic, thereby making it possible to determine the acoustic transfer function of the material around the ½ harmonic.

In this case, the parasitic mixing properties will be advantageously used to determine the mechanical properties, i.e. the non-fluid properties of the part.

Figure 4:
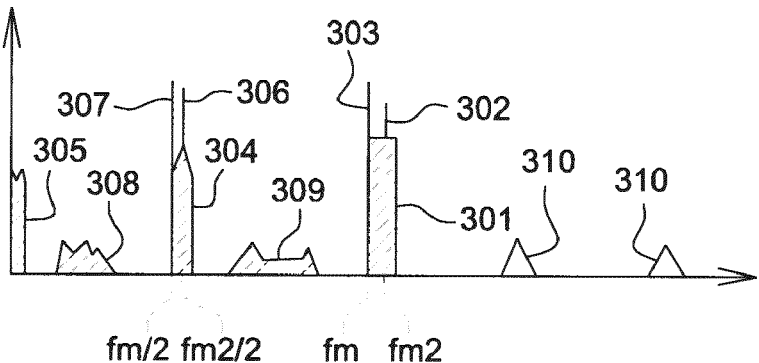
FIG. 4: an illustration of the spectrum of the reflected wave in the case of a dual-frequency set-up corresponding to the diagram shown in FIG. 1b in which one of the frequencies is modulated.

FIG. 4 illustrates these phenomena by a schematic representation of a spectrum of mechanical frequencies of a part.

A frequency 303 corresponds to the first mechanical vibration at the frequency $f_m$ and another frequency 302 corresponds to the second mechanical vibration at the frequency $f_{m2}$, which is modulated by an M-sequence 301.

Moreover, because of the presence of a cavity containing a liquid, mechanical vibrations of half frequencies 306, 307 are highlighted together with the white noise modulation multiplied by the transfer function of the fluid (a known result in the context of linear systems), denoted by 304 in the diagram shown in FIG. 4.

Furthermore, close to the zero frequency, a mixing product 305, characterized by $\pm m \times f_{m1} \pm n \times f_{m2}$ gives the mechanical transfer function around the zero frequency. This results from the fact that, by mixing, the white noise is transferred to the zero frequency and undergoes a temporal convolution by the mechanical transfer function of the structure 1.

The measured signal may in certain circumstances exhibit spectral lines 308, 309 outside the spectrum directly associated with the mechanical excitation.

Such lines are due to the separation of small droplets from the free surface of the liquid in the cavity, the kinetics of which small droplets are specific to each droplet. Such lines 308, 309 are characteristic and are advantageously used to improve the way in which the presence of liquid is detected.

Finally, other lines 310 of purely parasitic type are sometimes observed, these corresponding predominantly to non-linearities of the structure.

Thus, using the method, by analyzing the spectrum of the reflected wave 18 it is possible to detect, owing to the presence of certain lines 306, 307, 304, 305, 308 in said spectrum, the presence of a liquid 11 in cavities 12.

A device according to the invention for detecting the presence of a liquid 11 in at least one cavity 12 of a structure 1, such as a so called honeycomb core sandwich structure, comprises:

- first means 10, 13, 40, 41 for generating at least one vibratory mechanical excitation wave 14, 42 in the structure 1;
- second means 21, 22 for generating an incident electromagnetic wave 17 in a zone of the structure 1 in which the presence of a liquid is sought;
- third means 15, 19 for measuring an electromagnetic wave 18 reflected by the structure 1 receiving the incident wave 17; and
- fourth, processing and/or display means 20 capable of demonstrating the presence in a spectrum of the reflected wave 18 of at least one spectral line characteristic of an induced wave 16 on a surface of a liquid 11 contained in a cavity 12 of the structure 1 by the mechanical excitation wave 14, 42.

The first means advantageously comprise an actuator 10 in contact with said structure.

The actuator 10 is supplied by a power source 13 preferably delivering a sinusoidal signal of frequency $f_m$, said frequency preferably lying within the acoustic frequency range.

Furthermore, when the first means generate an excitation wave at the frequency $f_{m2}$ different from $f_m$, which may be modulated, said first means advantageously comprise a second actuator 40 in contact with the structure 1, said second actuator being supplied by a generator 41 delivering the signal at the frequency $f_{m2}$.

Such actuators 10, 40 are advantageously produced in a known manner using piezoelectric technology and are supplied by voltage sources corresponding to the excitation signals that have to be applied to the structure.

Preferably, the actuators 10, 40 are excited in a continuous regime in order to sustain the induced wave 16, which are rapidly damped.

The second means, for generating the incident electromagnetic wave 17, essentially comprise a radiofrequency generator 22 and an antenna 21 which is designed to radiate in the direction of the zone of the structure 1 that has to be analyzed, a priori close to one or both of the actuators 10, 40 producing the mechanical excitation wave 14, 42.

The third means, for measuring the reflected electromagnetic wave 18, essentially comprise an antenna 15 and means 19 for demodulating said reflected wave that are capable of establishing a frequency spectrum of said wave.

In a particularly inexpensive embodiment, the means 19 for demodulating the reflected electromagnetic wave 18 essentially consist of a simple self-oscillatormixer.

The emitting antenna 21 of the second means and/or the receiving antenna 15 of the third means are preferably directional antennas, it being possible for one and the same antenna to both emit the incident wave 17 and receive the reflected wave 18.

The directivity of said second and/or third means makes it possible to define the zone of the structure 1 under investigation and therefore to locate the position in said structure of the cavities 12 containing a liquid 11 when the presence of liquid is detected.

The fourth means 20 consist of any means for processing the spectrum of the reflected electromagnetic wave 18, making it possible to demonstrate one of the effects signifying with a high probability the presence of a liquid 11 in a cavity 12 of the structure 1.

In an embodiment having minimal data processing, the spectrum is presented in a graphical form, thereby enabling an experienced operator to interpret the various lines of the spectrum within the context of an investigation in progress.

Preferably, the signal is processed, for example after sampling by a computer unit, in order to allow automatic detection of lines in the spectrum of the reflected wave 18 signifying the presence of liquid in a cavity.

In this case, a situation corresponding to a probable presence of liquid is indicated by a display, optionally together with an audible signal for drawing the attention of an operator, the display and/or the audible signal preferably being modulated so as to provide information about the amount of liquid that may be present in the zone undergoing measurement by the device, it being possible for such information to be deduced from the relative intensities of the various lines of the reflected wave spectrum.

In one particular embodiment, means (not shown), for example a system for depositing an ink by micronozzles, are associated with the device so as to deposit colored marks, for example with an ink having a color in contrast with the surface of the structure, and being able to be easily removed, on zones detected as containing liquid in cavities. Such a marking device thus makes it possible to scan, by means of the device, large areas of the structure without interrupting a search phase and, in a subsequent processing phase, to be able to instantly identify the zones potentially containing liquid in order to carry out a more detailed local examination or to carry out the draining operations that are generally necessary in order to remove the liquid from the structure.

Figure 5:
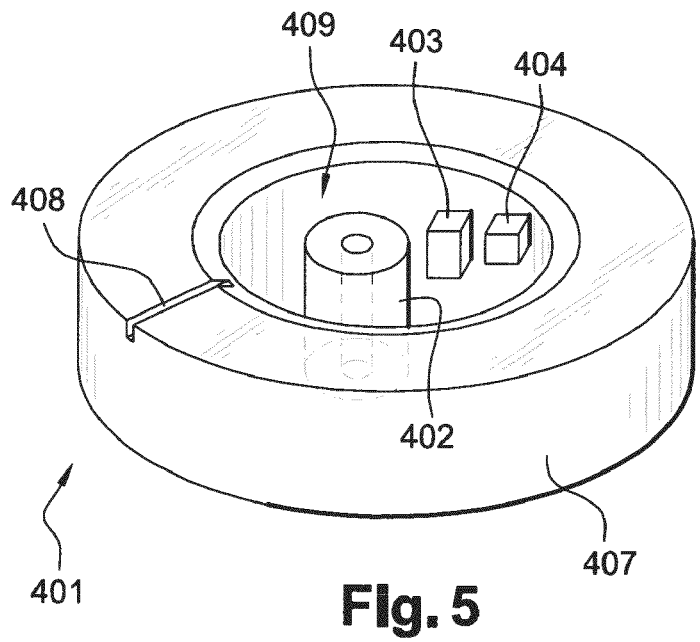
FIG. 5: a schematic illustration of a probe combining acoustic and radar functions for a device according to the invention.

One embodiment, which is particularly advantageous economically and from the operational standpoint, is shown in FIG. 5 for producing a compact probe 401 suitable for the device and for implementing the method, capable of carrying out the mechanical excitation, electromagnetic radiation and electromagnetic measurement functions.

The compact probe 401 of the device comprises a torus 407, which is not completely symmetrical, produced in piezoelectric technology, which is connected to frequency generators that generate frequencies corresponding to the mechanical excitation frequencies $f_m$ and $f_{m2}$ as seen above.

It is known that a torus made of piezoelectric materials supports two degenerate vibrational modes, i.e. modes having the same frequency. This property is only true if the symmetry is perfect.

When the symmetry is broken, the torus is capable of resonating at two frequencies $f_m$ and $f_{m2}$ that are close together but separate. A weight or a grove 408 is generally sufficient to break the symmetry of the torus 407.

Remaining inside the torus is a space 409 sufficient to install, if this should prove to be advantageous, i.e. if because of their size or their thermal dissipation it is not desirable to install them elsewhere, the following:

- the antenna 402 used for transmitting and receiving the electromagnetic waves 17, 18. The antenna 402 consists, for example, of an open coaxial cable, as illustrated in FIG. 5, which is capable of radiating in the frequency range in question, from a patch or a resonant cavity (whether iris-coupled or not) or any other suitable antenna;

all or part of the electronics for the frequency generator and of the electronics for amplifying the signal for supplying the piezoelectric component;

all or part of the supply electronics for the antenna for emitting the incident electromagnetic wave 17;

all or part of the electronics for the electromagnetic detection part 403, for example a self-oscillator mixer or else an oscillator connected to a mixer; and all or part of the signal processing electronics 404.

A device may therefore be produced that uses a small lightweight probe that can be easily moved up to the surface of a structure in order to detect the presence of liquid, particularly water, in cavities of the structure.

Said device is capable of detecting water in liquid form in panels of the honeycomb core sandwich type having carbon-fiber-based skin panels, but not exclusively in such panels, including through a metallization mesh when such a mesh covers one of the skin panels, in general on the side of the more accessible face of the panel.

The device makes it possible to seek the presence of water not only in the factory but also, because it can be made to have a sufficiently small size, to be used without removing an installed part, for example on an aircraft.

The invention claimed is:

1. A method for detecting the presence of a liquid in a cavity of a structure, comprising the steps of:
    subjecting said structure to a mechanical vibration by an excitation wave generated by an excitation wave generation device;
    subjecting a zone of said structure, in which the presence of the liquid in said cavity is sought, to an incident electromagnetic wave generated by an electromagnetic wave generation device;
    receiving a reflected electromagnetic wave from elements of the structure in the zone; and
    analyzing said reflected electromagnetic wave to deduce therefrom the presence or absence of said liquid in said cavity of said structure by a signal processor as a function of modulations induced by the mechanical vibration on characteristics of said reflected electromagnetic wave.

2. The method of claim 1, further comprising the step of generating one component of said excitation wave by an approximately sinusoidal vibratory excitation of frequency $f_m$ to initiate an oscillation or an induced wave at the surface of said liquid in said cavity at a subharmonic frequency of the excitation frequency $f_m$.

3. The method of claim 2, further comprising the step of generating another component of the excitation wave by a vibratory excitation of frequency $f_{m2}$ shifted relative to the frequency $f_m$.

4. The method of claim 3, further comprising the step of modulating a frequency of one of the components of the excitation wave.

5. The method of claim 4, further comprising the step of modulating the frequency by a white or pseudo-white noise.

6. The method of claim 1, further comprising the step of detecting predefined spectral lines in a spectrum of said reflected electromagnetic wave by said signal processor to deduce the presence of said liquid in said cavity of said structure.

7. The method of claim 6, further comprising the step of detecting at least one predefined spectral line in the spectrum of said reflected electromagnetic wave corresponding to at least one of the following: subharmonic of frequency $f_{m2}/2$ of an excitation frequency $f_m$ or subharmonic of frequency $f_{m2}/2$ of an excitation frequency $f_{m2}$.

8. An apparatus for detecting the presence of a liquid in a cavity of a structure, comprising:
    an excitation wave generation device to generate at least one vibratory mechanical excitation wave in the structure;
    an electromagnetic wave generation device to generate an incident electromagnetic wave in a zone of the structure in which the presence of said liquid is sought;
    a measuring device to detect and measure a reflected electromagnetic wave from the zone of the structure receiving the incident electromagnetic wave; and
    a signal processor to process said reflected electromagnetic wave reflected and to provide information relating to the presence of said liquid in a spectrum of said reflected electromagnetic wave of at least one spectral line characteristic of an induced wave on a surface of said liquid contained in the cavity of the structure by said mechanical excitation wave.

9. The apparatus of claim 8, wherein said signal processor generates audible signal modulated to provide information about the amount of said liquid present in the cavity of the structure.

10. The apparatus of claim 8, further comprising a display to display said spectrum of said reflected electromagnetic wave.

11. The apparatus of claim 8, wherein said excitation wave generation device comprises a first actuator in contact with the structure and a power source to generate and supply a sinusoidal mechanical excitation wave at frequency a frequency $f_m$ to said first actuator.

12. The apparatus of claim 11, wherein said excitation wave generation device further comprises a second actuator in contact with the structure and a generator to supply a sinusoidal signal at a frequency $f_{m2}$ shifted relative to the frequency $f_m$.

13. The apparatus of claim 8, further comprising a probe with a mechanically vibrating piezoelectric technology based torus to generate said mechanical excitation wave at a frequency $f_m$, or at a frequency $f_m$ and at a frequency $f_{m2}$ shifted relative to the frequency $f_m$.

14. The apparatus of claim 13, wherein a hollow part of said torus comprises at least one of the following:
    an antenna to emit and receive electromagnetic waves;
    all or part of supply electronics for piezoelectric components of said torus;
    all or part of said electromagnetic wave generation device to emit said incident electromagnetic wave;
    all or part of said measuring device to detect and measure said reflected electromagnetic wave; and
    all or part of said signal processor.

15. The apparatus of claim 8, wherein said electromagnetic wave generation device comprises a radio frequency generator to generate said incident electromagnetic wave and an antenna to radiate said incident electromagnetic wave in the direction of the zone of the structure.

16. The apparatus of claim 8, wherein said measuring device comprises an antenna to detect and receive said reflected electromagnetic wave and a demodulator to demodulate and establish a frequency spectrum of said reflected electromagnetic wave.

* * * * *